(12) United States Patent
Lee

(10) Patent No.: US 10,499,899 B2
(45) Date of Patent: Dec. 10, 2019

(54) MEDICAL TUBE FIXING APPARATUS

(71) Applicant: Zionmed Co., Ltd., Seoul (KR)

(72) Inventor: Suk-Il Lee, Seoul (KR)

(73) Assignee: Zionmed Co., Ltd., Seoul (KR)

( * ) Notice: Subject to any disclaimer, the term of this patent is extended or adjusted under 35 U.S.C. 154(b) by 448 days.

(21) Appl. No.: 15/315,862

(22) PCT Filed: Dec. 24, 2015

(86) PCT No.: PCT/KR2015/014255
§ 371 (c)(1),
(2) Date: Dec. 2, 2016

(87) PCT Pub. No.: WO2017/014378
PCT Pub. Date: Jan. 26, 2017

(65) Prior Publication Data
US 2017/0189587 A1    Jul. 6, 2017

(30) Foreign Application Priority Data
Jul. 20, 2015   (KR) .................. 10-2015-0102628

(51) Int. Cl.
*A61B 17/04* (2006.01)
*A61M 1/00* (2006.01)
*A61M 25/02* (2006.01)

(52) U.S. Cl.
CPC .......... *A61B 17/04* (2013.01); *A61B 17/0401* (2013.01); *A61M 1/00* (2013.01);
(Continued)

(58) Field of Classification Search
CPC .. A61M 2025/0266; A61M 2025/0286; A61B 17/04; A61B 17/0401; A61B 17/064
See application file for complete search history.

(56) References Cited

U.S. PATENT DOCUMENTS 3,677,250 A * 7/1972 Thomas ................. A61M 25/02
                                                    128/DIG. 26
4,074,397 A * 2/1978 Rosin .................... A61M 25/02
                                                    128/DIG. 15
(Continued)

FOREIGN PATENT DOCUMENTS

KR      10-1064844 B1      9/2011
KR      20-0474714 Y1     10/2014
KR      10-1535899 B1      7/2015

OTHER PUBLICATIONS

Korean Search Report dated Apr. 8, 2016; for PCT/KR2015/014255; 3 pages.

*Primary Examiner* — Susan S Su
(74) *Attorney, Agent, or Firm* — Daly Crowley Mofford & Durkee, LLP

(57) ABSTRACT

The present disclosure relates to a medical tube fixing apparatus which includes an adhesive member for securing the medical tube. The medical tube is inserted into the incised surgical site of the patient to discharge blood, body fluids, and the like to the outside. The surgical site where the medical tube is inserted is sutured with staples or suture threads. The adhesive member is made of a strip or band shaped tape-like material. The adhesive member is fixedly coupled at one end to the staple or the suture thread which sutures the patient's skin, and adheres to the outer surface of the medical tube to fix the medical tube together with the staple or suture. An operator can quickly and conveniently fix the medical tube to the patient's skin using the adhesive member. It is easy to manufacture the medical tube fixing apparatus, and manufacturing cost can be reduced.

5 Claims, 13 Drawing Sheets

(52) U.S. Cl.
CPC .......... *A61M 1/008* (2013.01); *A61M 1/0086* (2014.02); *A61M 2025/0286* (2013.01)

(56) References Cited

U.S. PATENT DOCUMENTS

| | | | | |
|---|---|---|---|---|
| 4,221,215 A | * | 9/1980 | Mandelbaum | A61M 16/047 128/DIG. 26 |
| 4,569,348 A | | 2/1986 | Hasslinger | |
| 4,683,895 A | * | 8/1987 | Pohndorf | A61B 17/0644 248/505 |
| 5,002,563 A | * | 3/1991 | Pyka | A61B 17/06 606/222 |
| 5,300,037 A | | 4/1994 | Delle et al. | |
| 5,382,239 A | * | 1/1995 | Orr | A61M 25/02 604/177 |
| 5,637,098 A | * | 6/1997 | Bierman | A61M 25/02 128/DIG. 26 |
| 5,792,115 A | * | 8/1998 | Horn | A61M 25/02 604/174 |
| 5,868,132 A | | 2/1999 | Winthrop et al. | |
| 6,247,211 B1 | * | 6/2001 | Bell | A61M 25/02 24/298 |
| 7,799,000 B2 | * | 9/2010 | Silich | A61M 25/02 604/174 |
| 9,642,987 B2 | * | 5/2017 | Bierman | A61M 25/02 |
| 2003/0055382 A1 | * | 3/2003 | Schaeffer | A61M 25/02 604/179 |
| 2003/0216694 A1 | * | 11/2003 | Tollini | A61M 25/02 604/174 |
| 2005/0076921 A1 | * | 4/2005 | Rozier | A61M 25/02 128/877 |
| 2007/0265571 A1 | * | 11/2007 | Utterberg | A61M 25/02 604/174 |
| 2008/0249476 A1 | * | 10/2008 | Bierman | A61M 25/02 604/175 |
| 2009/0137961 A1 | * | 5/2009 | Bracken | A61M 25/02 604/177 |
| 2009/0299294 A1 | * | 12/2009 | Pinkus | A61M 25/02 604/177 |
| 2009/0306603 A1 | * | 12/2009 | Bierman | A61M 25/02 604/180 |
| 2010/0022962 A1 | * | 1/2010 | Bierman | A61M 25/02 604/180 |
| 2010/0179482 A1 | * | 7/2010 | Wright | A61M 25/02 604/178 |
| 2011/0118670 A1 | * | 5/2011 | Kay | A61M 25/02 604/177 |
| 2014/0088568 A1 | * | 3/2014 | Brennan | A61M 27/00 604/541 |
| 2015/0313593 A1 | * | 11/2015 | Patenaude | A61B 17/085 602/43 |
| 2016/0287846 A1 | * | 10/2016 | Lee | A61M 39/08 |
| 2018/0318554 A1 | * | 11/2018 | Karim | A61M 25/02 |

* cited by examiner

MEDICAL TUBE FIXING APPARATUS

CROSS-REFERENCE TO RELATED APPLICATION

This application is a U.S. National Stage Application of International application No. PCT/KR2015/014255, filed on Dec. 24, 2015. This application claims priority to and benefit of Korean Patent Application No. 10-2015-0102628, filed on Jul. 20, 2015 before the Korean Intellectual Property Office (KIPO), the disclosures of which are incorporated by reference in their entirety herein.

BACKGROUND

1. Technical Field

The present disclosure relates to a medical tube fixing apparatus, and more particularly to a medical tube fixing apparatus by which a medical tube can be easily fixed by using a band-shaped adhesive member, which may allow to obtain the same results regardless of a practitioner and to reduce the operation time and the risk of infection after surgery.

2. Discussion of the Related Art

In general, after patients have been treated in a surgery, body fluids such as blood or pus may be caught inside of the patient's body. In this case, a drainage apparatus is used, which allows the medical staff to quickly discharge the body fluids generated in the patient's organs to the outside for quick recovery of the patient.

In the drainage apparatus, a medical tube for discharging the body fluids to the outside is fastened and used. The medical tube may include widely used ones which are a catheter used for discharging bile or abscess from the liver or stomach to the outside of the human body, a urethral catheter inserted into the bladder for discharging the excrements, or a drain tube for discharging the body fluid generated in the internal organs of the patient to the outside in a state that its one part is inserted into the human body and its other part is exposed to the outside of the body.

In recent years, a medical skin stapler has been widely used for sealing a surgical site in a state where the medical tube is inserted after a patient's operation is completed. The medical skin stapler, meaning a device for sealing the skin using staples, is an improvement of the conventional method in which an incised site of the skin is sealed with a suture thread and a needle at the time of a surgical operation or a cosmetic surgery. The staple used in the skin stapler has a substantially ⊏ shape. The staple is loaded on a cartridge of the skin stapler, and both ends of the staple are bent inward to seal the skin when it is pushed by and released from the skin stapler. In order to fix the medical tube exposed to the outside in such a sealed state, it is fixed to the skin using a method of directly tying it with a thread to a general medical band or the skin.

However, the medical band has a problem that the adhesive strength is weakened when it is used for a long time and therefore it should be frequently replaced. It also has a problem that a gap is grown between the medical band and the medical tube whenever the patient moves and the adhesive force becomes weakened, which causes the medical tube to be pushed out to the outside.

There is also a problem that the medical tubing may be detached and organs of the patient may be damaged due to insufficient adhesive force of the medical band. There are also other problems such as occurrence of infection due to leakage of pleural fluid caused by the detachment of the medical tube, and induction of emphysema of the lung due to air infiltration.

In addition, the fixing method of tying with the thread is not robust, so that the medical tube can be moved and thus the medical tube inserted into the inside of the patient's body can be released to the outside.

In view of these points, there is a prior art which is Korean Patent Registration No. 10-1064844 (published on Sep. 14, 2011) entitled "A Medical Tube Fixing Apparatus."

However, the fixing apparatus for the medical tube has the following disadvantages. A fixed cap, a tube guide member, a tape, and the like must be separately manufactured, so that the manufacturing cost will be increased. In addition, it takes a long time to install the fixing apparatus of the medical tube fixed by the tape on the patient, and it is not fixed firmly during long-term use.

In addition, since the tape directly adheres to the skin, inflammation or the like may be caused during repeated use for a long period of time. The fixing apparatus is expensive to use because it is used as a disposable medical apparatus due to the nature of the medical apparatus attached directly to the patient's body and because when the fixing apparatus of the medical tube is replaced, the whole apparatus must be replaced.

SUMMARY

The present disclosure is directed to providing a medical tube fixing apparatus which can easily fix a medical tube to obtain the same result regardless of a practitioner.

The present disclosure is also directed to providing a medical tube fixing apparatus which can shorten the operation time and reduce the risk of infection after surgery.

In addition, the present disclosure is directed to providing a medical tube fixing apparatus using a medical adhesive member.

According to exemplary embodiments of the present disclosure, a medical tube fixing apparatus may include an adhesive member which is coupled to a staple and adheres to an outer surface of a medical tube. By fixing the medical tube to the staple using the adhesive member, the fixing operation of the medical tube becomes simpler and easier, so that the same result can be obtained irrespective of the practitioner. The risk of infection after surgery can be reduced.

According to exemplary embodiments of the present disclosure, there is provided a medical tube fixing apparatus, including: a staple for suturing an incised site of a patient's skin into which a medical tube is inserted; and an adhesive member, being fixed at one end to a center of the staple and adhering to an outer surface of the medical tube, for fixing the medical tube to the staple.

In an exemplary embodiment of the present disclosure, the adhesive member may be formed in a strip or band shape extending by a predetermined length in a longitudinal direction of the medical tube, and be adhesively wound around the outer surface of the medical tube in a plurality of turns in a spiral shape along the longitudinal direction.

In an exemplary embodiment of the present disclosure, the adhesive member may include a first portion fixedly coupled to a center of the staple and a second portion extending from the first portion in a direction perpendicular to the medical tube by a predetermined length so as to form a bent strip or band shape, and be adhesively wound in a horizontal direction around the outer surface of the medical tube at least one time.

In an exemplary embodiment of the present disclosure, the adhesive member may include a main adhesive portion, extending in a longitudinal direction of the medical tube by a predetermined length, for adhering to the outer surface of the medical tube in the longitudinal direction; a fixing portion having one end of the main adhesive portion fixedly coupled to the center of the staple; a first auxiliary adhesive portion, extending from both sides of the main adhesive portion adjacent to the fixing portion in opposite horizontal directions, for adhesively wrapping the outer surface of the medical tube in the horizontal direction; and a second auxiliary adhesive portion, positioned above the first auxiliary adhesive portion and extending from both sides of the main adhesive portion in opposite horizontal directions, for adhesively wrapping the outer surface of the medical tube in the horizontal.

In an exemplary embodiment of the present disclosure, the adhesive member may include a transparent or semi-transparent tape; an adhesive formed on one side of the tape and adhering to the outer surface of the medical tube; and a release paper which is attached to the adhesive and is removed when adhering to the outer surface of the medical tube.

According to other exemplary embodiments of the present disclosure, there is provided a medical tube fixing apparatus to be used with a suture thread.

The medical tube fixing apparatus may include a suture thread, being joined to a needle, for suturing an incised site of a patient's skin into which a medical tube is inserted; and an adhesive member, being provided in a strip or band shape and fixedly coupled to the suture thread at one end, for adhesively wrapping an outer surface of the medical tube together with the suture thread a plurality of times outside the skin sutured by the suture thread, and fixing the medical tube by the suture thread.

In an exemplary embodiment of the present disclosure, the adhesive member may include a stopper for engaging with one end of the suture thread in the longitudinal direction of the suture thread.

In another exemplary embodiment, the adhesive member may include a stopper for engaging with one end of the suture thread in the width direction of the suture thread.

As described above, the medical tube fixing apparatus of the present disclosure can be easily manufactured, thereby reducing the manufacturing cost of it and the medical cost burden on the patient. In addition, with the medical tube fixing apparatus it is possible to fix the medical tube at the same time as sealing the incised surgical site. Therefore, the operator can quickly and conveniently install it.

Further, the medical tube fixing apparatus of the present disclosure can shorten the operation time and reduce the risk of postoperative infection by fixing the medical tube using staples, suture threads, and the like.

In addition, the medical tube fixing apparatus of the present disclosure can provide the same result regardless of the practitioner by easily fixing the medical tube using the adhesive member.

In addition, the present disclosure provides the medical tube fixing device in various forms using staples, suture threads, and the like, thereby fixing the medical tube to be suitable for an incised skin at the time of surgery.

DETAILED DESCRIPTION OF THE EMBODIMENTS

Figure 1:
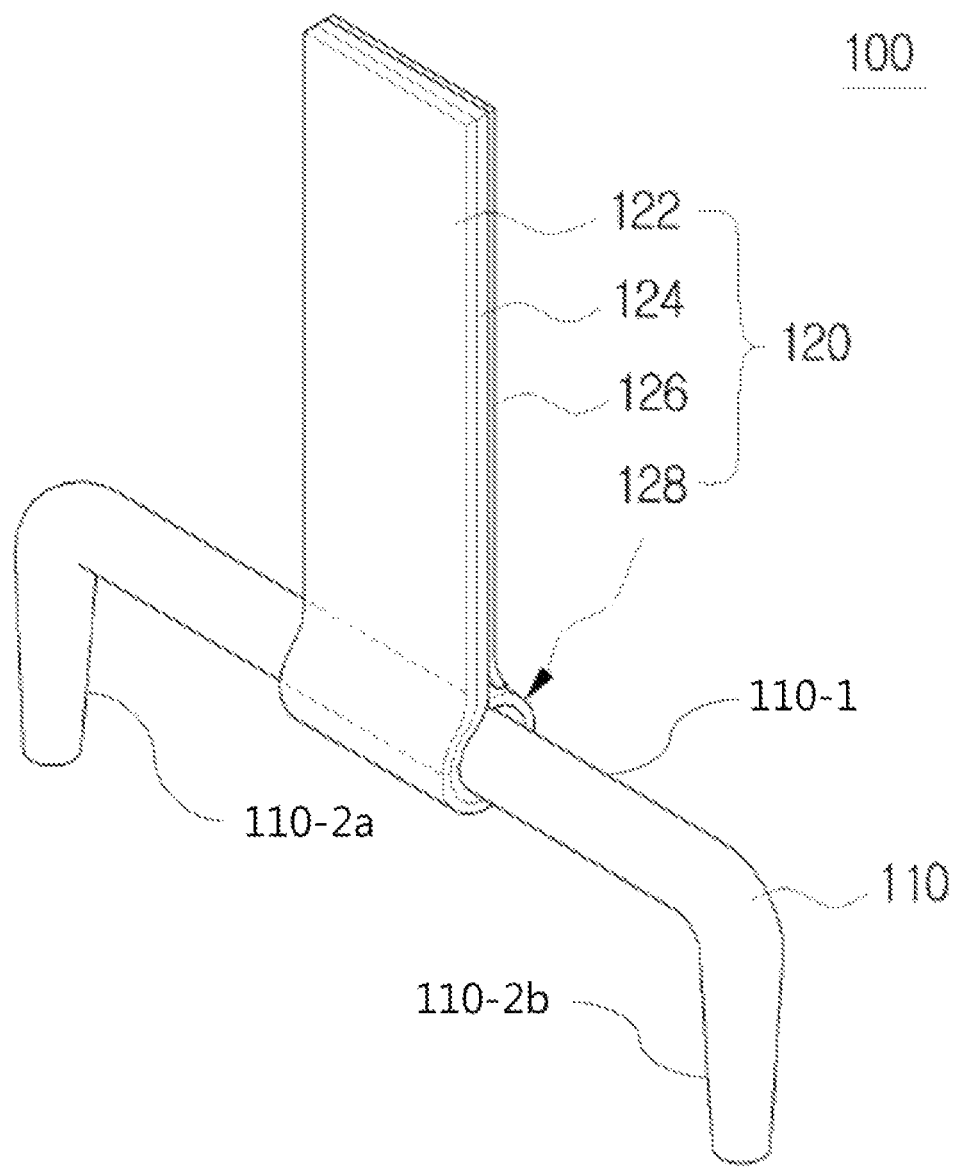
FIG. 1 illustrates a configuration of a medical tube fixing apparatus according to a first exemplary embodiment of the present disclosure.

The embodiments of the present disclosure may be modified into various forms, and the scope of the present disclosure should not be construed as being limited by the embodiments described below. The present embodiments are provided to enable those skilled in the art to more fully understand the present disclosure. Accordingly, the shape and the like of the elements shown in the drawings may be exaggerated in order to emphasize a clearer description.

Hereinafter, embodiments of the present disclosure will be described in detail with reference to FIGS. 1 to 11.

Figure 2:
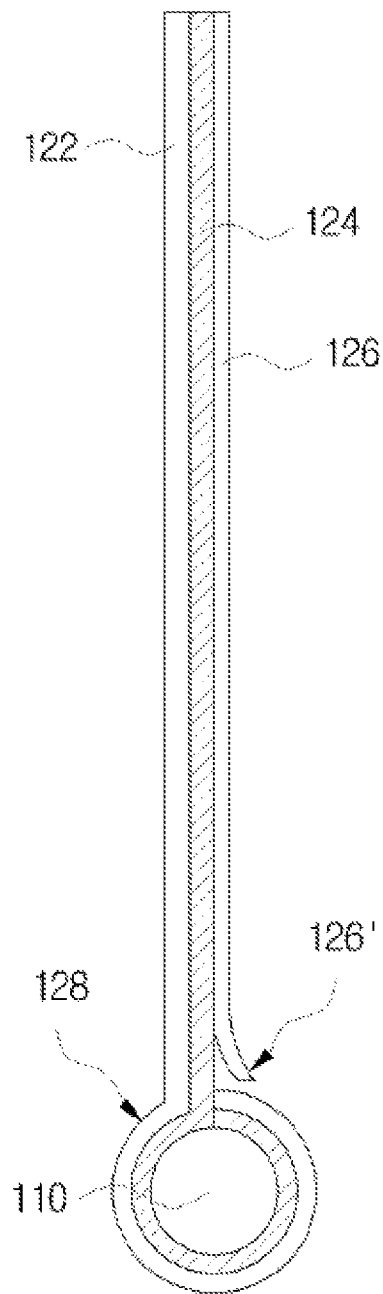
FIG. 2 is a sectional view showing a configuration of the medical tube fixing apparatus shown in FIG. 1.

FIG. 1 is a view showing a configuration of a medical tube fixing apparatus according to a first exemplary embodiment of the present disclosure. FIG. 2 is a cross-sectional view showing the configuration of the medical tube fixing apparatus shown in FIG. 1, and FIG. 3 is a view showing a state in which the medical tube is fixed using the medical tube fixing apparatus shown in FIG. 1.

Figure 3:
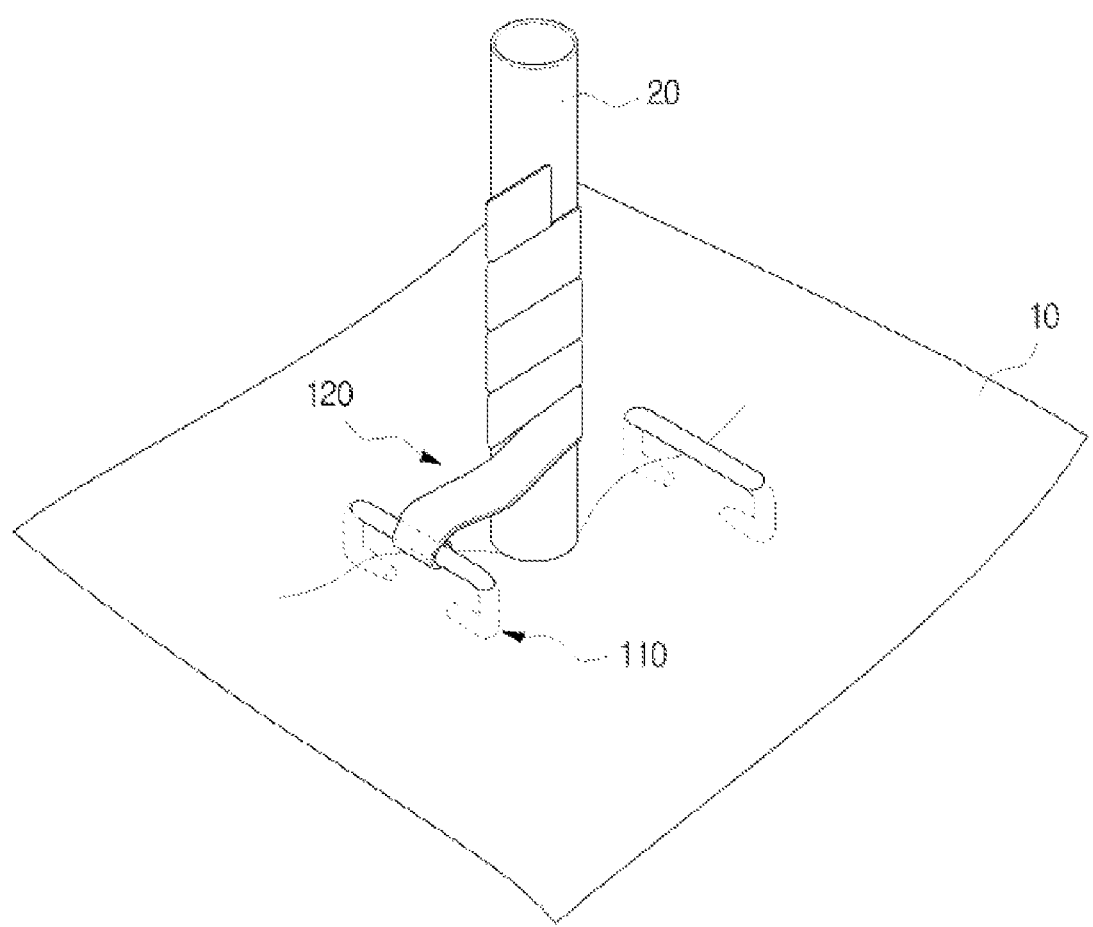
FIG. 3 is a view showing a state where the medical tube is fixed using the medical tube fixing apparatus shown in FIG. 1.

Referring to FIGS. 1 to 3, a medical tube fixing apparatus 100 according to the first exemplary embodiment of the present disclosure is to fix a medical tube 20 for quickly discharging a blood tube, a body fluid, and the like generated in a lesion or an affected part of a patient to the outside when the patient is operated.

A staple 110 includes a flat top crown 110-1 and two legs 110-2*a* and 110-2*b* extending from both ends of the flat top crown to be perpendicular to the flat top crown. When the medical tube 20 is inserted into the surgical site of the patient, the medical tube fixing apparatus 100 couples the adhesive member 120 to the staple 110 that seals the surgical site where the medical tube 20 is inserted, attaching the adhesive member 120 to the outer circumferential surface of the medical tube 20 so as to firmly fix the medical tube 20 to the patient's skin.

Specifically, in an exemplary embodiment, the medical tube holding apparatus 100 of this embodiment may include the staple 110 and the adhesive member 120.

The staple 110 may be fastened to the periphery of the patient's affected part of into which the medical tube 20 is inserted, for example, using a skin stapler or the like to seal the incised surgical site.

The adhesive member 120 may be provided with a strip- or band-shaped medical adhesive tape having a predetermined length and width. In an exemplary embodiment, the adhesive member 120 may include a tape 122, an adhesive 124 adhering to one surface of the tape 122, and a release paper 126 adhering to the other surface of the adhesive 124. The adhesive member 120 is provided with a fixing portion 128, one end of which is fixedly coupled to the center of the staple 110.

In an exemplary embodiment, the tape 122 may be made of a transparent or semitransparent material such as a resin film, a fiber material, or the like. The tape 122 may be made of a material having an elastic force.

In an exemplary embodiment, the adhesive 124 may be made of a double-sided adhesive tape that its one side adheres to one surface of the tape 122 and the release paper 126 is attached to its other side. The other side of the adhesive 124 may be coated. The adhesive 124 may be made of an adhesive material of which adhesive force is not affected by the body temperature of the patient. The adhesive 124 may adhere to the outer circumferential surface of the medical tube 20 by a detachable adhesive material. The adhesive 124 may be made of an adhesive material such as an acrylic adhesive, a rubber adhesive, a urethane adhesive, or a silicone adhesive for use in medical bandages and tapes. These adhesive materials are already well known in the art, so a detailed description of them would not be given here.

In an exemplary embodiment, the release paper 126 may adhere to the coated surface of the adhesive 124 to protect an adhesive force of the adhesive 124. A partial portion 126' of the release paper 126 may be separated from the adhesive 124 so as to be easily separated from the coated surface of the adhesive 124 when the adhesive member 120 adheres to the outer circumferential surface of the medical tube 20. When the adhesive member 120 adheres to the outer surface of the medical tube 20, the release paper 126 is removed.

In an exemplary embodiment, one end of the adhesive member 120, which forms the fixing portion 128, may be fixedly coupled to the center of the staple 110. The fixing portion 128 may be fixedly coupled to the staple 110 by the adhesive 124 and the tape 122.

In an exemplary embodiment, the adhesive member 120 may be formed in the strip or band shape extending in the longitudinal direction of the medical tube 20 by a predetermined length as shown in FIG. 3. The adhesive member 120 may be adhesively wound around and along the outer surface of the medical tube 20 plural times in the form of spiral.

Therefore, the medical tube fixing apparatus 100 of this embodiment may be is so configured that when the medical tube 20 is inserted into the inside of the surgical site of the patient, the adhesive member 120 fixedly coupled to the staple 110 can adhere to the medical tube 20 while wrapping the medical tube 20 along the outer circumferential surface of the medical tube 20 plural times in the form of spiral.

The medical tubing fixing apparatus 100 can easily fix the medical tube 20 to the skin 10 of the patient using at least one staple 110, which seals the incised surgical site adjacent the medical tubing 20, and the adhesive member 120.

Figure 4:
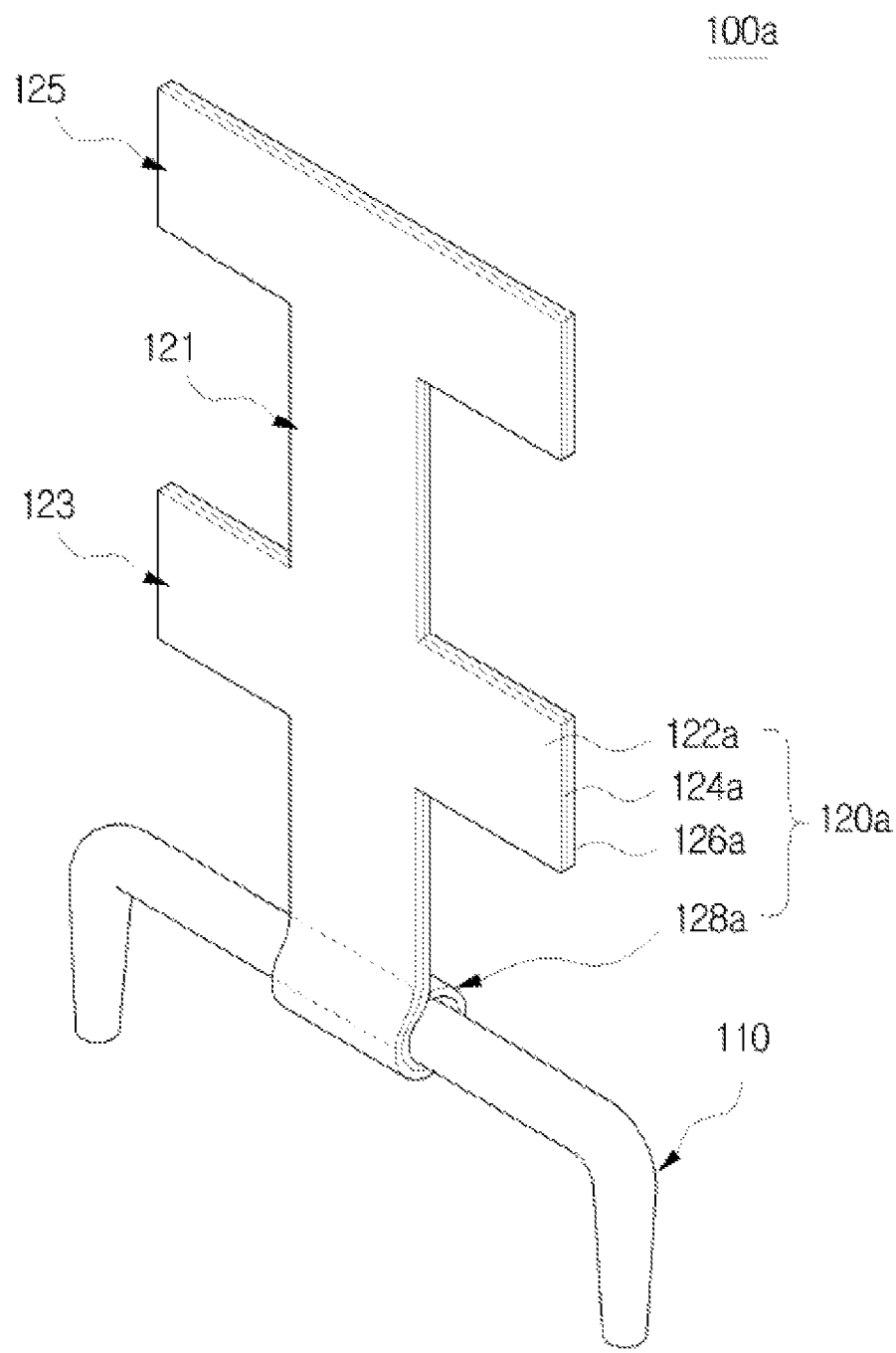
FIG. 4 illustrates a configuration of a medical tube fixing apparatus according to a second exemplary embodiment of the present disclosure.
Figure 5:
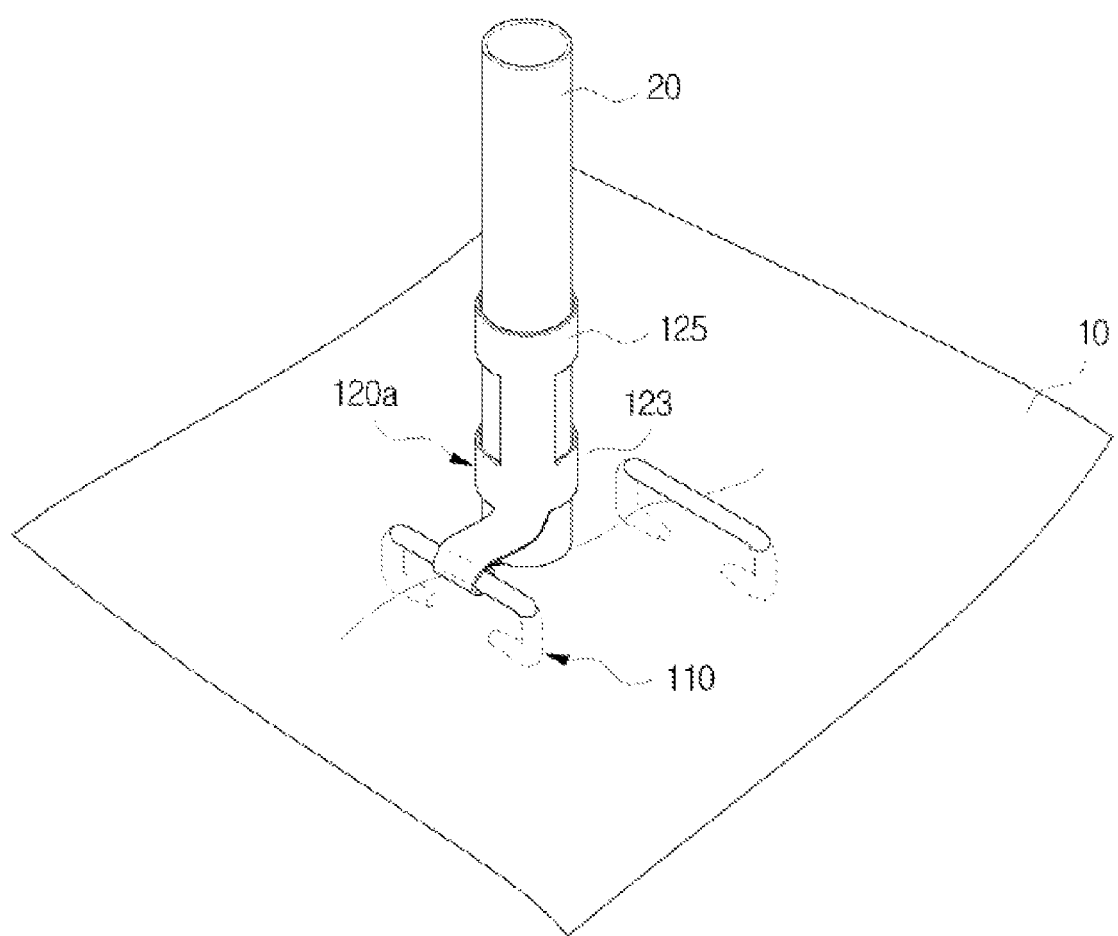
FIG. 5 is a view showing a state where the medical tube is fixed using the medical tube fixing apparatus shown in FIG. 4.

FIG. 4 is a view showing a configuration of a medical tube fixing apparatus according to a second exemplary embodiment of the present disclosure, and FIG. 5 is a view showing a state in which a medical tube is fixed using the medical tube fixing apparatus shown in FIG. 4. Here, description of the elements of which functions are the same as or similar to those in the first exemplary embodiment will be omitted.

With reference to FIGS. 4 and 5, a medical tube fixing apparatus 100a according to an exemplary embodiment may include a staple 110 for sealing or suturing the incised skin 10 of the patient near the medical tube 20 inserted into the patient's skin 10, and an adhesive member 120a, being fixedly coupled to the center of the staple 110 and adhering to the outer circumferential surface of the medical tube 20, for fixing the medical tube 20 to the staple 110.

Unlike the first embodiment, the adhesive member 120a of this embodiment may include a main adhesive portion 121 adhering to the medical tube 20 in the longitudinal direction of the medical tube 20, and first and second auxiliary adhesive portions 123 and 125, each of which extends in opposite horizontal directions from both lateral ends of the main adhesive portion 121, for adhesively wrapping upper and lower positions of the medical tube 20 adjacent to the staple 110, respectively.

In an exemplary embodiment, the adhesive member 120a may be formed by sequentially laminating a tape 122a, an adhesive 124a and a release paper 125a so as to have the same sectional structure as that of the first exemplary embodiment. A fixing portion 128a which is fixedly coupled to the center of the staple 110 may be formed at an end of the adhesive member 120a.

The main adhesive portion 121 is extended in the longitudinal direction of the medical tube 20 by a predetermined length and adheres to the outer surface of the medical tube 20 in the longitudinal direction. Here, the fixing portion 128a is disposed at one end of the main adhesive portion 121.

In an exemplary embodiment, the first auxiliary adhesive portion 123 may be formed by the portions which extend from both lateral ends of the main adhesive portion 121 adjacent to the fixing portion 128a in both opposite horizontal directions, respectively. The first auxiliary adhesive portion 123 is attached to the outer surface of the medical tube 20 while horizontally and adhesively wrapping the outer circumferential surface of the medical tube 20.

The second auxiliary adhesive portion 125 may be spaced apart from the first auxiliary adhesive part 123 by a predetermined distance and may be formed by the two portions, extending from the other both lateral ends of the main adhesive portion 121 in opposite horizontal directions, respectively, so that they can adhesively wrap the outer circumferential surface of the medical tube 20 in the horizontal direction.

Therefore, the medical tube fixing apparatus 100a of this embodiment can firmly fix the medical tube 20 by the first and second auxiliary adhesive portions 123 and 125 as shown in FIG. 5.

Figure 6:
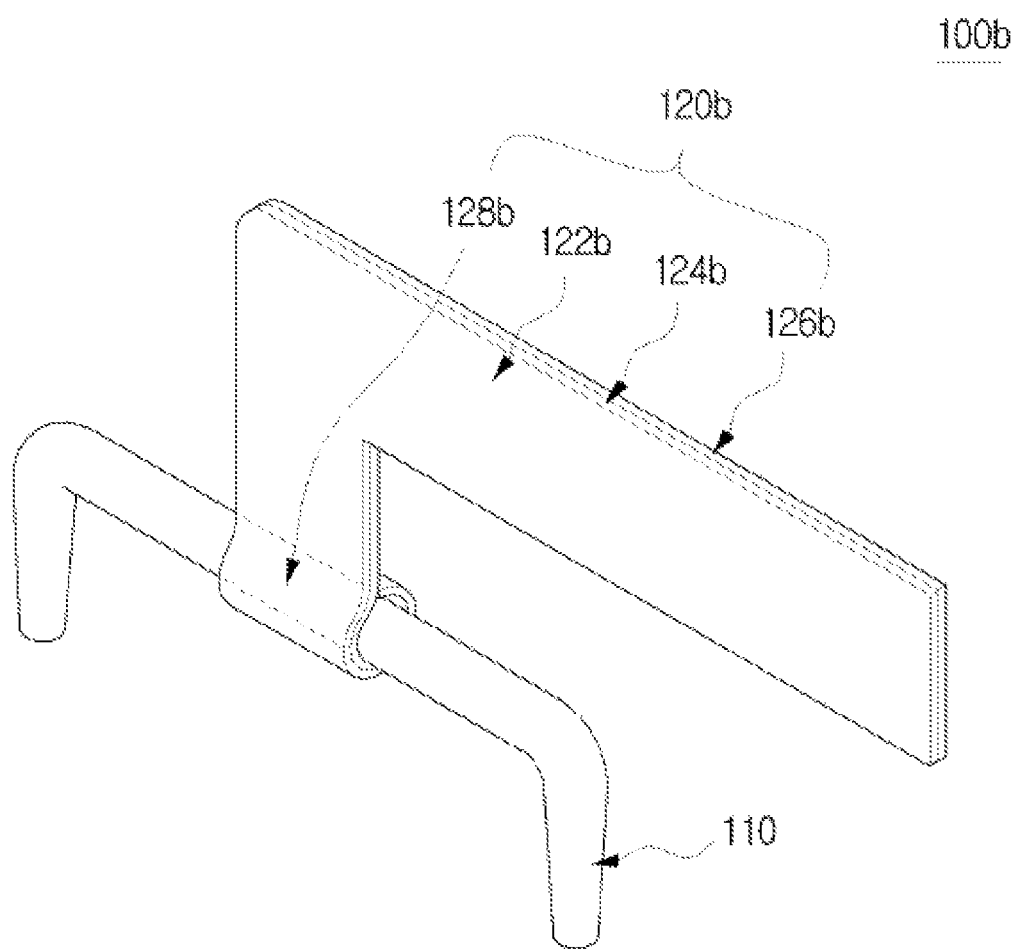
FIG. 6 illustrates a configuration of a medical tube fixing apparatus according to a third exemplary embodiment of the present disclosure.
Figure 7:
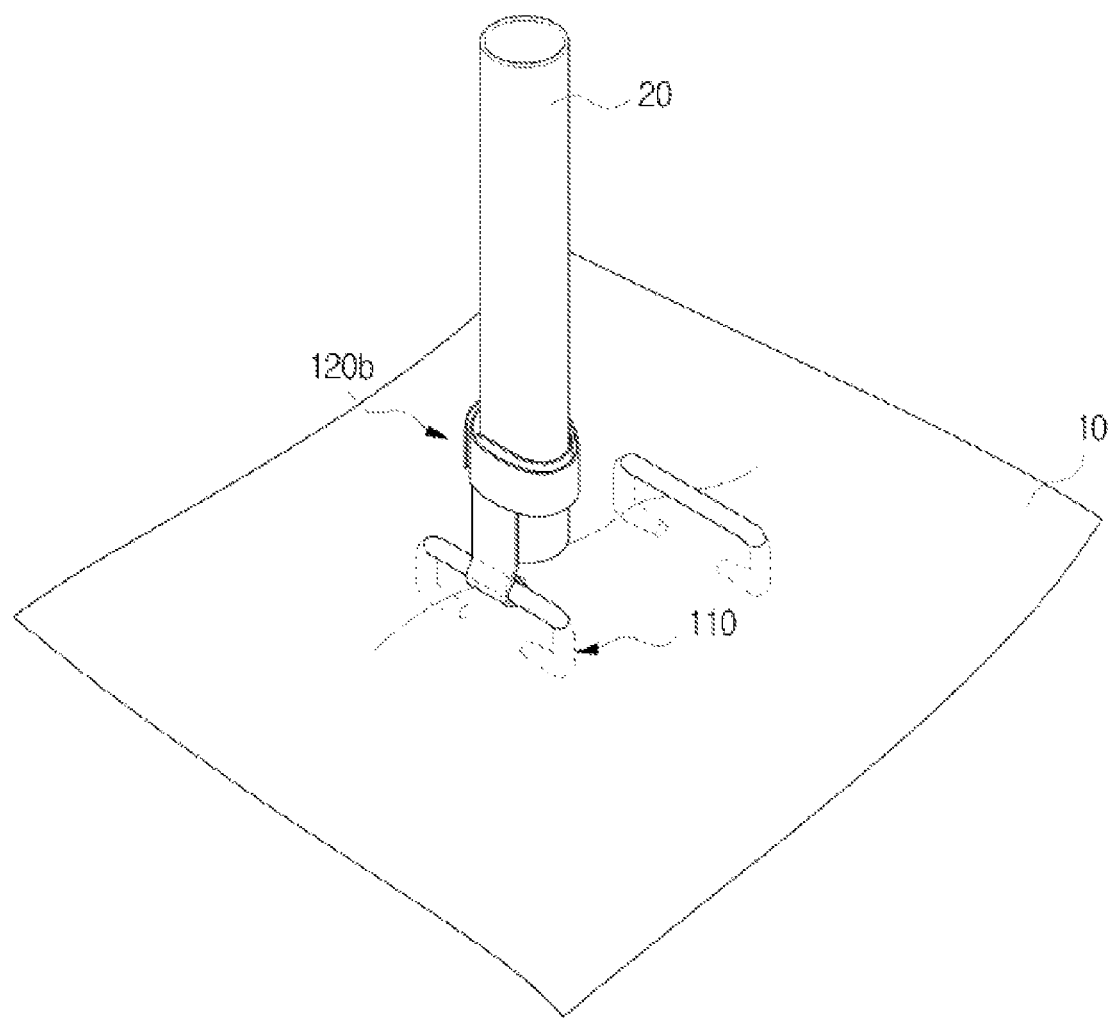
FIG. 7 is a view showing a state where the medical tube is fixed using the medical tube fixing apparatus shown in FIG. 6.

FIG. 6 illustrates a configuration of a medical tube fixing apparatus according to a third embodiment of the present disclosure, and FIG. 7 shows a state in which the medical tube is fixed using the medical tube fixing apparatus shown in FIG. 6. Here, description of the elements of which functions are the same as or similar to those in the first embodiment will be omitted.

Referring to FIGS. 6 and 7, the medical tube fixing apparatus 100b of this embodiment may include a staple 110 and an adhesive member 120b. The adhesive member 120b may have a shape bent at a right angle, and include a fixing portion 128b for being fixedly coupled to the center of the staple 110, and a band-shaped portion bent from the fixing portion 128b in a direction perpendicular to the medical tube 20 and extended by a predetermined length.

The adhesive member 120b may be formed by sequentially laminating a tape 122b, an adhesive 124b and a release paper 125b so as to have the same sectional structure as that of the first embodiment. The adhesive member 120b may have, at an end, a fixing portion 128b which is fixedly coupled to the center of the staple 110.

As shown in FIG. 7, in the medical tube fixing apparatus 100b of this embodiment the adhesive member 120b may be adhesively wound around the outer surface of the medical tube 20 at least once in the horizontal direction.

The medical tube fixing apparatuses 100, 100a and 100b of the first to third embodiments described above can firmly fix the medical tube 20 to the patient's skin 10 using the staple 110.

Figure 8:
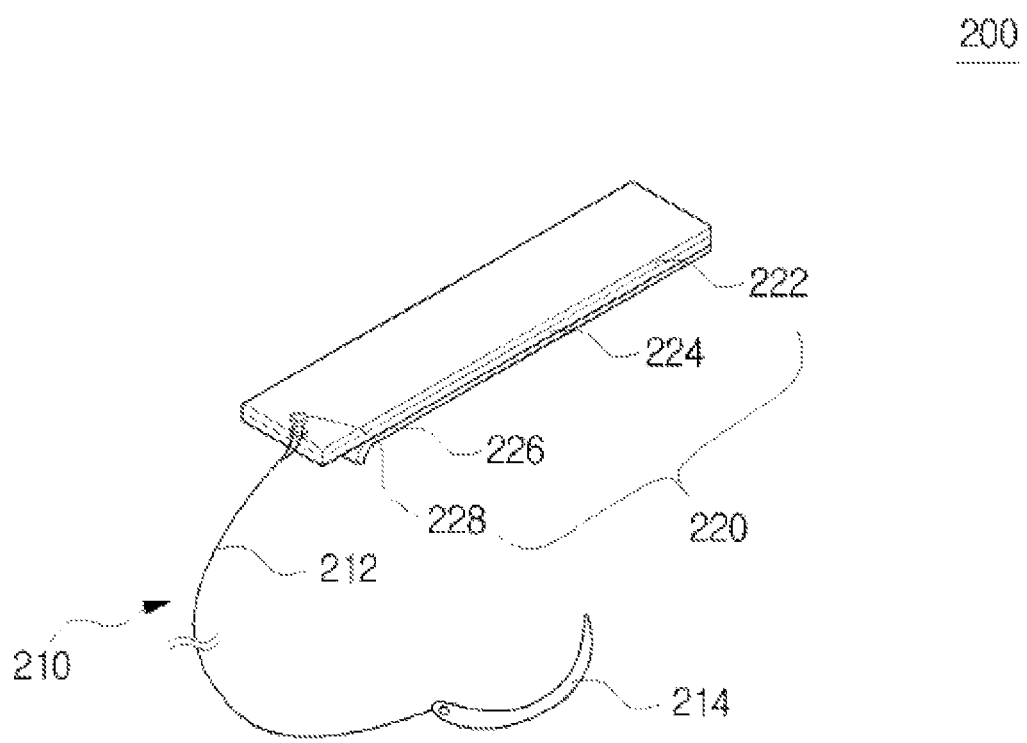
FIG. 8 illustrates a configuration of a medical tube fixing apparatus according to a fourth exemplary embodiment of the present disclosure.
Figure 9A:
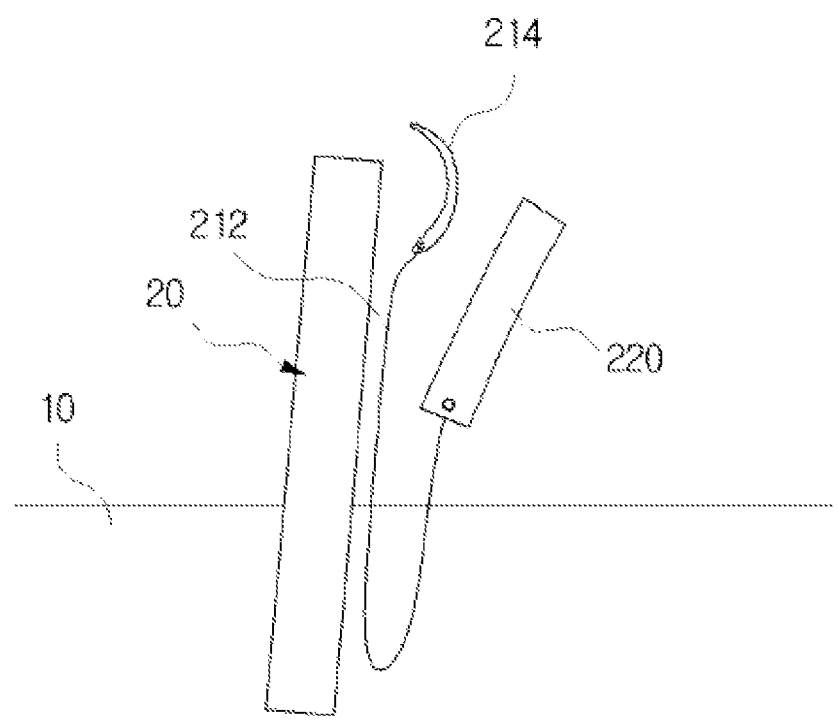
FIG. 9A and FIG. 9B are views showing a state where the medical tube is fixed using the medical tube fixing apparatus shown in FIG. 8.
Figure 9B:
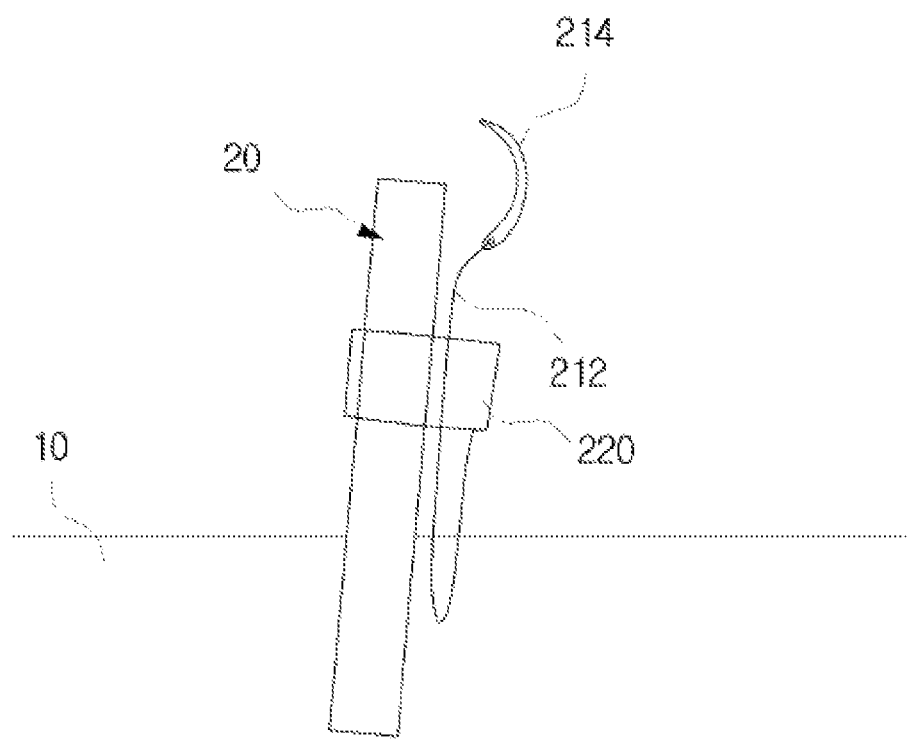

FIG. 8 illustrates a configuration of a medical tube fixing apparatus according to a fourth embodiment of the present disclosure. FIGS. 9A and 9B are views showing a state in which the medical tube is fixed using the medical tube fixing apparatus shown in FIG. 8.

Referring to FIGS. 8 to 9B, the medical tube fixing apparatus 200 of this embodiment may fix the medical tube 20 using a suturing member 210.

To this end, the medical tube fixing apparatus 200 may include the suturing member 210 and an adhesive member 220.

The suturing member 210 may include a needle 214 and a suture thread 212. The needle 214 is coupled to one end of the suture thread 212 and the adhesive member 220 is fixedly coupled to the other end. The suturing member 210 can suture the incised skin near the medical tube 20 inserted into the patient's skin 10.

In an exemplary embodiment, the adhesive member 220 may be provided in a strip or band shape. One end of the adhesive member 220 may be fixedly connected to the suture thread 212. The adhesive member 220 may adhesively wrap the outer surface of the medical tube 20 along with the suture thread 212 plural times outside of the surgical site of the skin 10 sutured by the suture thread 212. This adhesive member 220 can fix the medical tube 20 to the patient's skin 10 by fixing the medical tube 20 to the suture thread 212. In this embodiment, the adhesive member 220 may be coupled to the other end of the suture thread 212 in the longitudinal direction of the suture thread 212.

In an exemplary embodiment, the adhesive member 220 may be made of a medical adhesive tape having a strip or band shape and a predetermined length and width. The adhesive member 220 may include a tape 222, an adhesive 224 bonded to one surface of the tape 222, a release paper 226 attached to the other surface of the adhesive 224, and a stopper 228 with which the suture thread 212 is coupled. The stopper 228 may be made of, for example, a hardened material and be fixed to the center of one end of the adhesive member 220. The stopper 228 may function to couple the suture thread 212 with the adhesive member 220, and to prevent the adhesive member 220 from being inserted into the patient's skin 10 by being followed by the suture thread 212 when the patient's incised skin 10 is sealed using the suturing member 210.

Therefore, as shown in FIGS. 9A and 9B, the medical tube fixing apparatus 200 of this embodiment may be configured such that the incised site of the patient's skin 10 is sutured with the suture thread 212 and the needle 214. Then, the medical tube 20 may be wrapped plural times together with the suture thread 212 to be fixed by the adhesive member 220.

Figure 10:
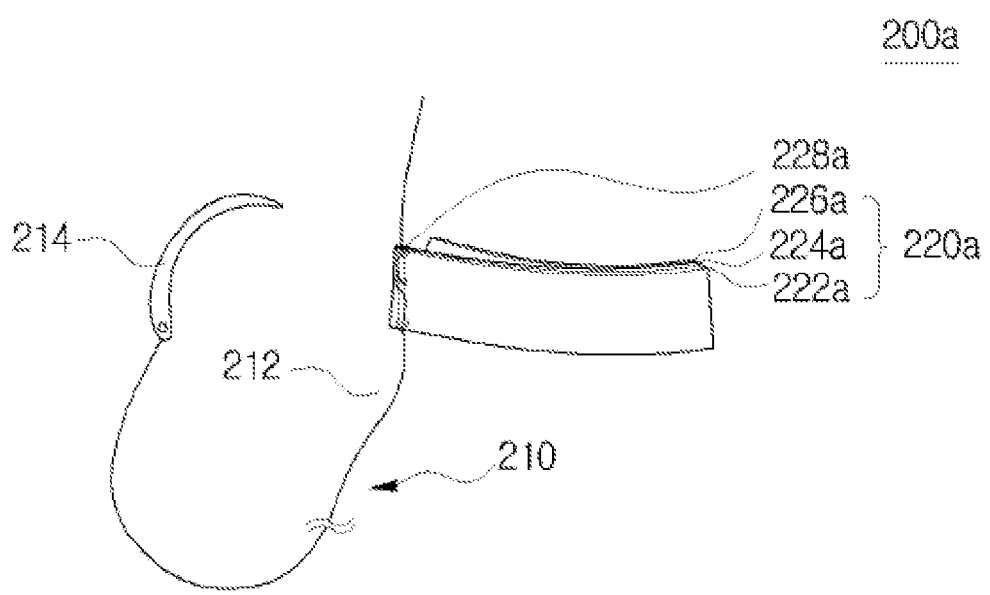
FIG. 10 illustrates a configuration of a medical tube fixing apparatus according to a fifth exemplary embodiment of the present disclosure.
Figure 11A:
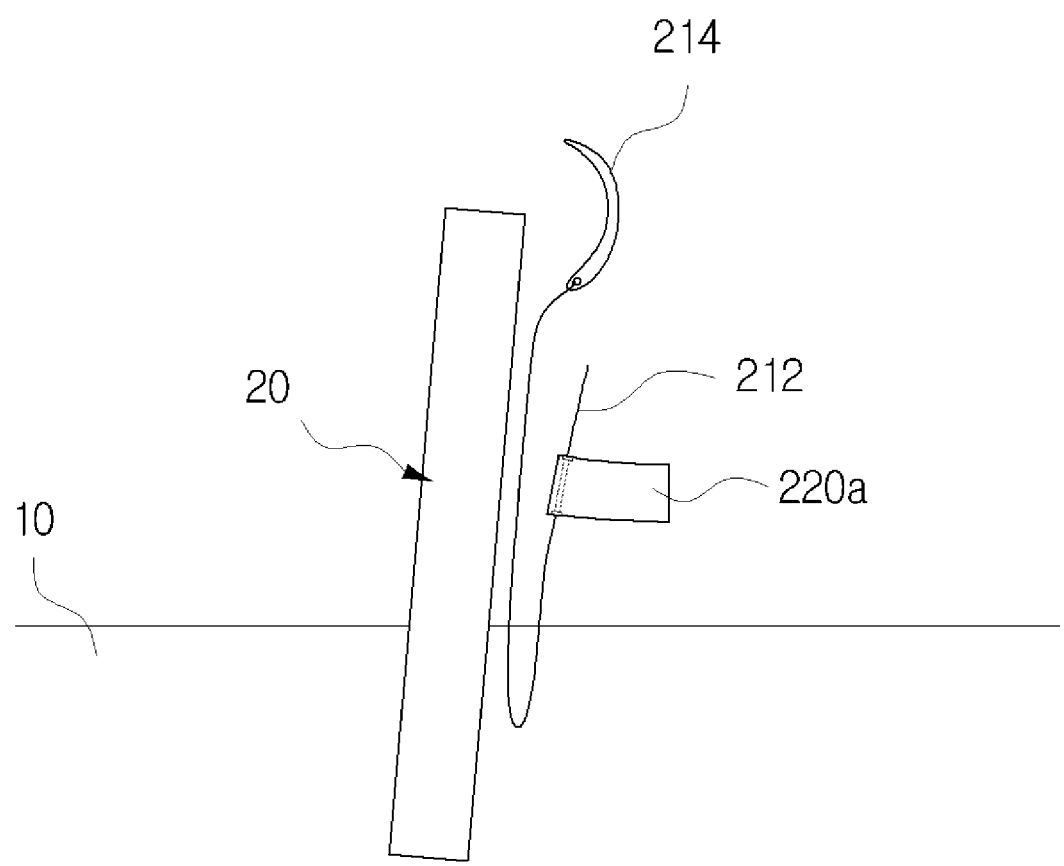
FIG. 11A and FIG. 11B are views showing a state where the medical tube is fixed using the medical tube fixing apparatus shown in FIG. 10.
Figure 11B:
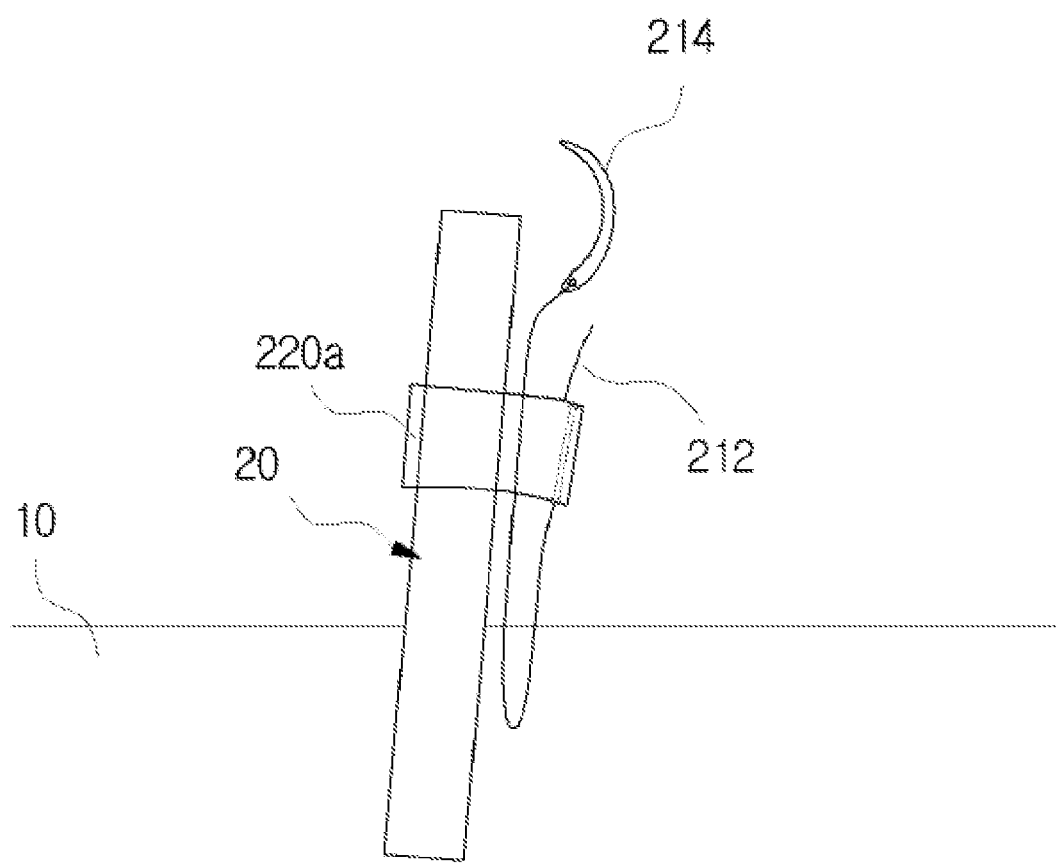

FIG. 10 is a view showing a configuration of a medical tube fixing apparatus according to a fifth exemplary embodiment of the present disclosure. FIG. 11A and FIG. 11B are views showing a state in which the medical tube is fixed using the medical tube fixing apparatus shown in FIG. 10.

With reference to FIGS. 10 to 11B, in the medical tube fixing apparatus 200a of this embodiment, the adhesive member 220a may be coupled horizontally at the center portion of the suture thread 212 unlike the fourth embodiment.

In an exemplary embodiment, the adhesive member 220a may be made of a medical adhesive tape having a strip or band shape and a predetermined length and width. The adhesive member 220a may include a tape 222a, an adhesive 224a, a release paper 226a, and a stopper 228a. The stopper 228a also provides materials, shapes, and functions that are generally similar to those in FIG. 8. However, the stopper 228a of this embodiment is fixed in the width direction at an end of the adhesive member 220a. The stopper 228a may be installed such that the adhesive member 220a can be fixed at a proper position of the suture thread 212. Here, the adhesive member 220a may be provided so as to be adjustable in its position along the longitudinal direction of the suture thread 212 by the stopper 228a.

Therefore, as shown in FIGS. 11A and 11B, the medical tube fixing apparatus 200 of this embodiment may be configured such that the incised site of the patient's skin 10 is sealed with the suture thread 212 and the needle 214. Then, the medical tube 20, together with the suture thread 212, may be adhesively wrapped plural times by the adhesive member 220a to fix the medical tube 20.

The medical tube fixing apparatuses 200 and 200a of the fourth and fifth embodiments described above can firmly fix the medical tube 20 to the patient's skin 10 using the suture thread 212.

The foregoing is illustrative of exemplary embodiments of the present inventive concept and is not to be construed as limiting thereof. Although a few exemplary embodiments have been described, those skilled in the art will readily appreciate that many modifications are possible in the exemplary embodiments without materially departing from the novel teachings and advantages of the present inventive concepts. Accordingly, all such modifications are intended to be included within the scope of the present inventive concepts as defined in the claims. Therefore, it is to be understood that the foregoing is illustrative of various exemplary embodiments and is not to be construed as limited to the specific exemplary embodiments disclosed, and that modifications to the disclosed exemplary embodiments, as well as other exemplary embodiments, are intended to be included within the scope of the appended claims.

What is claimed is:

1. A medical tube fixing apparatus, comprising:
   a staple comprising a flat top crown and a leg perpendicularly extending from each of both longitudinal ends of the flat top crown, the staple is capable of being fixed to a site of patient's skin into which a medical tube is inserted, by a skin stapler; and
   an adhesive member comprising a transparent or semi-transparent tape; an adhesive layer coated on one side of the tape; and a release paper attached to the adhesive layer and being capable of being released from the adhesive layer, the adhesive member being an elongated band having a longitudinal end fixedly coupled with the flat top crown of the staple, the other longitudinal end of the elongated band configured to adhesively wound around an outer surface of the medical tube at least one turn after the release paper is released from the adhesive, thereby fixing the medical tube to the staple.

2. A medical tube fixing apparatus, comprising:

a staple comprising a flat top crown and a leg perpendicularly extending from each of both longitudinal ends of the flat top crown, the staple is capable of being fixed to a site of patient's skin into which a medical tube is inserted, by a skin stapler; and an adhesive member, comprising a band-shaped main adhesive portion having a longitudinal end fixed to the flat top crown and extending in a direction perpendicular to the flat top crown by a predetermined length; and at least one band-shaped auxiliary adhesive portion extending from one lateral side or both lateral sides of the band-shaped main adhesive portion in one direction or in opposite two directions parallel to the flat top crown, wherein each of the band-shaped main adhesive portion and the at least one band-shaped auxiliary adhesive portion comprises a transparent or semi-transparent tape having an adhesive layer coated on one side of the tape and a release paper attached to the adhesive layer and capable of being released from the adhesive layer, wherein the band-shaped main adhesive portion is capable of being attached to the medical tube along an axial direction of the medical tube, and the at least one band-shaped auxiliary adhesive portion is capable of being wound around the medical tube in a circumferential direction of the medical tube.

3. A medical tube fixing apparatus, comprising:

a suture thread, being joined to a needle, for suturing an incised site of a patient's skin into which a medical tube is inserted; and an adhesive member, being provided in a strip or band shape and fixedly coupled to one end of the suture thread, for adhesively wrapping an outer surface of the medical tube together with the suture thread a plurality of turns outside the skin sutured by the suture thread, thereby fixing the medical tube to the suture thread.

4. The medical tube fixing apparatus according to claim 3, wherein the adhesive member comprises a stopper configured to be coupled with the one end of the suture thread and to prevent the adhesive member from being inserted into the incised site of the patient's skin.

5. The medical tube fixing apparatus according to claim 3, wherein the adhesive member comprises a transparent or semi-transparent tape; an adhesive layer coated on one side of the tape; and a release paper attached to the adhesive layer and capable of being released from the adhesive layer.

\* \* \* \* \*